US007335183B2

(12) United States Patent
Buiatti

(10) Patent No.: US 7,335,183 B2
(45) Date of Patent: Feb. 26, 2008

(54) NURSING AID SYSTEM

(75) Inventor: John Buiatti, Castaic, CA (US)

(73) Assignee: Aligned Innovation, Inc., Calabasas, CA (US)

( * ) Notice: Subject to any disclaimer, the term of this patent is extended or adjusted under 35 U.S.C. 154(b) by 243 days.

(21) Appl. No.: 10/662,659

(22) Filed: Sep. 15, 2003

(65) Prior Publication Data

US 2005/0059927 A1 Mar. 17, 2005

(51) Int. Cl.
*A61M 1/06* (2006.01)

(52) U.S. Cl. .......................................... 604/76; 604/74

(58) Field of Classification Search ............ 604/74–76, 604/346, 390, 391; 128/890
See application file for complete search history.

(56) References Cited

U.S. PATENT DOCUMENTS

| | | | | | |
|---|---|---|---|---|---|
| 751,415 | A | * | 2/1904 | Prindle | 128/890 |
| 4,799,922 | A | * | 1/1989 | Beer et al. | 604/74 |
| 5,415,620 | A | * | 5/1995 | Chen | 601/14 |
| 6,213,840 | B1 | * | 4/2001 | Han | 450/36 |
| 6,358,226 | B1 | * | 3/2002 | Ryan | 604/74 |
| 2002/0062103 | A1 | * | 5/2002 | Larsson et al. | 604/74 |
| 2003/0149398 | A1 | * | 8/2003 | Renz et al. | 604/74 |

* cited by examiner

*Primary Examiner*—Tatyana Zalukaeva
*Assistant Examiner*—Melanie J. Hand
(74) *Attorney, Agent, or Firm*—W. Norman Roth

(57) ABSTRACT

A nursing aid system which includes at least one breast cup and at least one nipple extender which may be integrally formed with the breast cup or which may comprise a separate piece. The breast cup has a concave breast receiving portion and a hollow generally cylindrical nipple receiving portion located on and projecting away from the breast receiving portion, the nipple receiving portion having a remote end which includes a milk delivery aperture. The nipple extender, if separately formed, may be slidably received in the nipple receiving portion of the breast cup and has an axial length less than the length of the nipple receiving portion. The nipple extender provides at least one flow channel for conducting milk from the mother's nipple to the milk delivery aperture and is preferably sized and configured to occupy most of the space in the nipple receiving portion of the breast cup which is not occupied by a mother's nipple.

12 Claims, 1 Drawing Sheet

NURSING AID SYSTEM

CROSS REFERENCE TO RELATED APPLICATIONS, IF ANY

None

BACKGROUND OF THE INVENTION AND PRIOR ART

The present invention relates to systems for assisting mothers to naturally breast feed babies. Mothers have often encountered pain from babies who pinch or bite their nipples during natural breast feeding. Breast shields have been designed to alleviate this common problem through the use of a flexible breast and nipple cover of sufficient thickness to substantially reduce flexing of the nipple portion and resultant pain encountered when breast feeding a biting baby. These breast shields effectively cover but do not extend the natural nipple and therefore fail to address the problem and frustration experienced by those mothers and their children who have not been able to effectively breast feed due to insufficient length, usually temporary, of the mother's nipple and resulting inability of the baby to effectively grasp it in its mouth for suckling.

OBJECT OF THE INVENTION

It is the primary object of the present invention to provide a nursing aid system which alleviates the above problem.

SUMMARY

Disclosed herein is a nursing aid system which includes at least one breast cup and at least one nipple extender which may be a separate part or which may be integrally formed with the breast cup. The breast cup has a concave breast receiving portion and a hollow generally cylindrical nipple receiving portion located on and projecting away from the breast receiving portion, the nipple receiving portion having a remote end which includes at least one milk delivery aperture which may be normally open or closed. The nipple extender may be integrally formed with or may be slidably received or otherwise positioned in the nipple receiving portion of the breast cup and has an axial length less than the length of the nipple receiving portion. The nipple extender is configured to provide at least one channel for conducting flow of milk from the mother's nipple to the milk delivery aperture and preferably occupies most of the space in the nipple receiving portion of the breast cup which is not occupied by a mother's nipple.

Although the system is designed to alleviate problems frequently encountered by humans, the teachings herein are not necessarily limited to human nursing.

DESCRIPTION OF THE PREFERRED EMBODIMENTS

Figure 1:
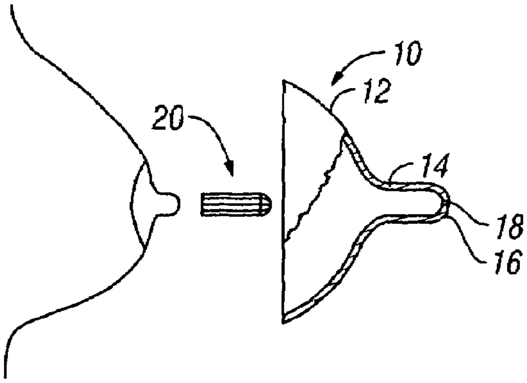
FIG. 1 is a schematic side elevation view, partly in cross section, of a nursing aid system pursuant to the invention comprised of a nipple cup and separately formed nipple extender.
Figure 2:
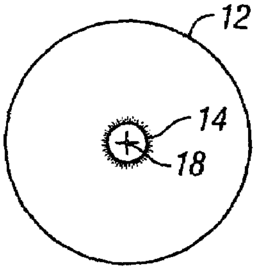
FIG. 2 is a front elevation view of the system of FIG. 1.

FIG. 1 depicts a breast cup 10 comprised of a generally concave breast receiving portion 12 having an integrally formed nipple portion 14 terminating in an end wall 16. The end is provided with a normally closed milk delivery aperture, such as a slit or crossed slits 18 preferably located in the end wall 16 as seen in FIG. 2. The entire breast cup 10 may be formed of flexible elastomeric material having a uniform wall thickness although the breast cup 1 may be configured with a variable wall thickness if desired. The flexible elastomeric material may be a silicone, latex or polyurethane material or mixtures thereof and may have a Shore A durometer hardness in the preferred range of 35-80. Those skilled in the art will readily understand that the flexibility of the breast cup 10 will depend not only upon the material and hardness but also upon the wall thickness, all of the properties being selected to insure that the cup may be comfortably retained against the breast and flexed to conform generally to the human breast configuration.

To accommodate human breasts having nipples of various natural lengths, one or more nipple extenders 20 of various sizes may be provided. A single nipple extender may be integrally formed with the breast cup or a number of separately fabricated nipple extenders may be provided in differing lengths, preferably all sized to be slid into and frictionally retained inside the nipple receiving portion 14 of the cup 10. FIG. 1 depicts the nipple extender 20 as a part separate form the cup 10 but those skilled in the art will understand that the nipple receiving portion 14 of the breast cup 10 shown in FIG. 1 can easily be fabricated with an increased wall thickness and centrally extending milk delivery passageway to effectively integrate the nipple extender 20 and cup 10. The integrally formed extender or separately formed extenders 20 should be sized and configured to occupy most and preferably substantially all space in the nipple receiving portion 14 of the cup 20 which would not ordinarily be occupied by a human nipple so as to accommodate natural nipples of different lengths and minimize the amount of air which must be first be ingested by a suckling infant before milk is delivered.

Figure 3:
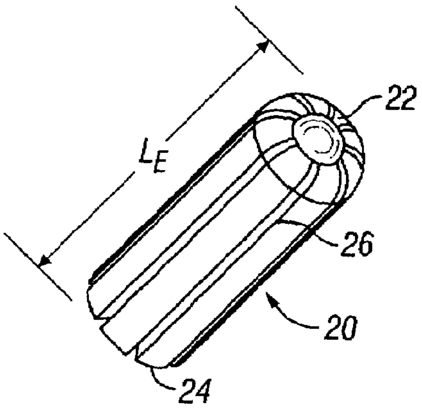
FIG. 3 is a perspective view of a presently preferred embodiment of a nipple extender showing a generally convex front end.
Figure 4:
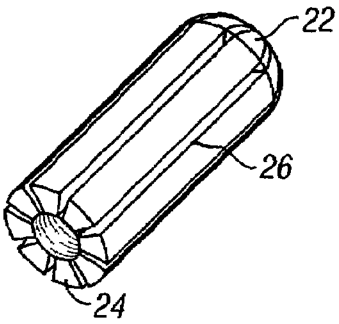
FIG. 4 is a perspective view of the presently preferred embodiment of a nipple extender of FIG. 3 showing a generally concave rear end.

FIGS. 3 and 4 show a first presently preferred embodiment of nipple extender 20 of generally cylindrical configuration having a rounded or hemispherical convex front end 22 as seen in FIG. 3 and a rear end 24 which preferably is configured with slight concavity as seen in FIG. 4. In this embodiment, at least one flow conducting groove 26 is provided. Preferably a series of peripherally spaced protuberances in the form of lands on the annular exterior surface of the extender 20 which engage the inside of the nipple receiving portion of the breast cup 10 provide a series of flow conducting grooves 26 between the lands for the flow of milk along the exterior of the nipple extender from the rear end 24 to the front end 22. The groove or grooves 26 terminate proximate the milk delivery aperture which, in the preferred embodiment shown, is a normally closed aperture formed by crossed slits 18. The inherent resilience of the breast cup 10 and the wall thickness of the nipple end wall 16 is selected to insure that suction provided by a nursing infant will easily open the flow conducting aperture in the end 16 in the nipple portion of the cup to conduct milk to the baby's mouth. The preferred configuration of nipple extender shown in FIGS. 3 and 4 with lengthwise extending grooves 26 on the annular surface of the nipple extender insures that the nipple extender 20 and grooves 26 can be easily and thoroughly cleaned when removed from the cup 10 and that air space in the cup 10 is also minimized to reduce the amount of air which must be ingested by the baby prior to drawing of milk through suckling.

Figure 6:
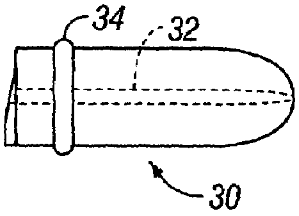
FIG. 6 is a side elevation view of a second embodiment of a nipple extender for use in the system of FIG. 1.

Although the presently preferred embodiment of nipple extender 20 may be configured as shown in FIGS. 3 and 4 with grooves 26 on its exterior surface to facilitate easy cleaning, such is not essential. A nipple extender 30 may be configured, for example, as shown in FIG. 6 with a single flow conducting passageway 32 which is preferably centrally located in the nipple extender 30. Alternatively, the nipple extender may have multiple flow passageways or be fabricated of a porous or open cell material to provide multiple milk flow channels.

Figure 5:
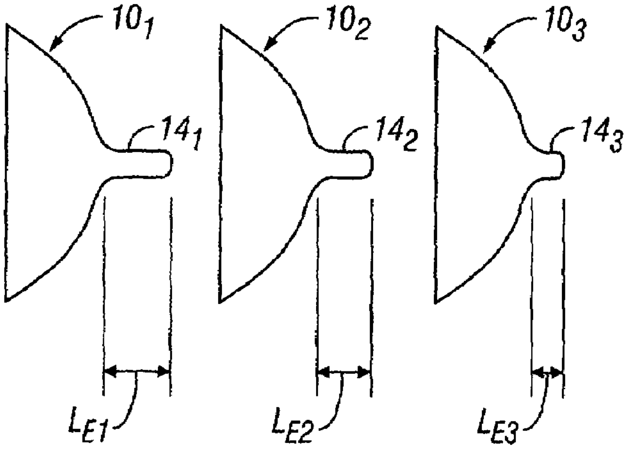
FIG. 5 is a schematic side elevation view showing a series of nipple cups having nipple portions of progressively reduced length.

In its broadest aspects, the system comprises a single breast cup 10 and nipple extender 20 which may either be a separate piece or which may be integrally formed with the breast cup as described above. Since separately formed nipple extenders can be removed from the breast cup for easier cleaning, it is currently contemplated that the system may best be produced and marketed in kit form comprising a few breast cups 10 each having a nipple portion length $L_{N1}$, $L_{N2}$, $L_{N3}$, etc. of gradually reducing length as shown in FIG. 5. Similarly, the nipple extenders 20 may be included in a series of different lengths $L_{E1}$, $L_{E2}$, $L_{E3}$, etc. (FIG. 3) to accommodate mothers having nipples of different natural lengths.

A mother who has difficulty in nursing her infant may then first select the breast cup 10 having the longest length nipple portion 14 which may be used with a nipple extender 20 of length correlated with the length of the nipple portion 14 of the cup 10 and with the natural length of the mother's nipple such that, in use, the nipple extender will occupy most and preferably substantially all space in the nipple receiving portion 14 which is not occupied by the mother's nipple. As the infant gets used to suckling with the longer nipples, the mother may gradually reduce the length of nipple to which the infant is exposed by changing cups and nipple extenders.

While the nipple extenders 20 and 30 preferably are retained in the nipple receiving portions 14 of the cup 10 by frictional engagement so that the extenders can be easily removed from the cups for cleaning, one or more annular protuberances, which may take the form of a collar or collars 34 as seen in FIG. 6, may be formed on the exterior annular surfaces of the nipple extenders 20 to assist in retaining the nipple extenders 20 in the nipple portions of the cups 10. Mating recesses or grooves may be formed in the interior of the nipple receiving portions 14 of the cups 10 to receive the protuberances so long as a suitable milk flow path is maintained. The protuberance need not take the form of an annular collar 34 as depicted FIG. 6. The protuberance may even take the form of a spiral male screw thread engageable with the interior surface of the nipple portion 14 of the breast cup 10. Simple sliding engagement of the nipple extenders 20, 30 with the interior surface of the nipple receiving portions 14 of the cups 10 is, however, presently is preferred.

Persons skilled in the art will readily appreciate that various additional modifications can be made from the presently preferred embodiments thus the scope of protection is intended to be defined only by the limitations of the appended claims.

The invention claimed is:

1. A nursing aid system comprising:

a breast cup having a concave breast receiving portion, said cup having a hollow generally cylindrical nipple receiving portion adapted for grasping by the mouth of an infant, said nipple receiving portion located on and projecting away from said concave portion, said nipple receiving portion having an end remote from said concave portion and a milk delivery aperature at said end; and a nipple extender axially slidably receiveable in said nipple receiving portion, said nipple extender having an axial length less than an axial length of said nipple receiving portion, said extender being sized and configured to occupy space in said nipple receiving portion not occupied by a mother's nipple, said extender having a flow channel for conducting milk in said nipple receiving portion from a mother's nipple to said milk delivery aperture, wherein said flow channel is provided on an exterior annular surface of said nipple extender, said flow channel extending from a first end of said extender to a location proximate said milk delivery aperture.

2. The nursing system of claim 1, wherein said flow channel is provided by multiple grooves on said annular surface.

3. The nursing system of claim 2, wherein said grooves extend parallel to a central axis of said generally cylindrical extender.

4. The nursing system of claim 1, wherein said breast cup is formed of flexible elastomeric material.

5. The nursing system of claim 4, wherein said milk delivery aperture comprises slit means extending through said end of said nipple receiving portion to provide a normally closed milk delivery aperture.

6. The nursing system of claim 5, wherein said slit means comprises crossed slits.

7. A nursing system comprising:

a series of breast cups each having a concave portion for receiving a female human breast, cups each having a hollow generally cylindrical nipple receiving portion adapted to be grasped by the mouth of an infant, said nipple receiving portion located on and projecting away from said concave portion, said nipple receiving portions of said series of cups being of different lengths and each having a milk delivery aperture in an end remote from said concave portion; and a series of generally cylindrical nipple extenders each axially slidably receiveable in said nipple receiving portions, said extenders each having an axial length less than an axial length of said nipple receiving portions, said extenders each being differently sized to occupy substantially all space in said nipple receiving portions not occupied by a human nipple, said extenders each having a channel for conducting milk in said nipple receiving portions from a human nipple to said milk delivery apertures, wherein said flow channels are provided on exterior annular surfaces of said nipple extenders, said flow channels extending from a first end of said extenders to a location proximate said milk delivery apertures.

8. The nursing system of claim 7, wherein said cups are formed of flexible elastomeric material.

9. The nursing system of claim 7, wherein said nipple extenders include spaced surfaces engaging said nipple receiving portions of said cups, said flow channels being between said spaced surfaces.

10. The nursing system of claim 9, wherein said spaced surfaces extend parallel to central axes of said nipple extenders.

11. The nursing system of claim 7, wherein said milk delivery apertures comprise slit means extending through said ends of said nipple receiving portions to provide normally closed milk delivery apertures.

12. The nursing system of claim 11, wherein said slit means comprises crossed slits.

* * * * *